United States Patent
Bardat

(10) Patent No.: US 8,252,227 B2
(45) Date of Patent: Aug. 28, 2012

(54) INVENTION RELATES TO A METHOD OF VIRAL INACTIVATION BY DRY HEATING

(75) Inventor: Annie Bardat, Limours (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 623 days.

(21) Appl. No.: 12/097,860

(22) PCT Filed: Dec. 19, 2006

(86) PCT No.: PCT/FR2006/002817
§ 371 (c)(1),
(2), (4) Date: Sep. 24, 2008

(87) PCT Pub. No.: WO2007/071845
PCT Pub. Date: Jun. 28, 2007

(65) Prior Publication Data
US 2009/0297398 A1    Dec. 3, 2009

(30) Foreign Application Priority Data
Dec. 19, 2005   (FR) ..................... 05 12875

(51) Int. Cl.
*A61L 11/00* (2006.01)
*C12N 13/00* (2006.01)
*A61M 1/14* (2006.01)

(52) U.S. Cl. ........ 422/1; 422/44; 435/173.1; 435/173.4; 435/173.5; 435/173.7

(58) Field of Classification Search ................ 422/1, 44; 435/173.1, 173.4–173.5, 173.7
See application file for complete search history.

(56) References Cited

U.S. PATENT DOCUMENTS

| | | | |
|---|---|---|---|
| 3,890,266 A * | 6/1975 | Serini et al. .................. | 524/611 |
| 5,831,027 A | 11/1998 | McIntosh et al. | |
| 2004/0023351 A1 * | 2/2004 | Grae ......................... | 435/173.5 |

FOREIGN PATENT DOCUMENTS

| | | |
|---|---|---|
| EP | 0094611 A | 11/1983 |
| EP | 0844005 A | 5/1998 |

* cited by examiner

Primary Examiner — Jill Warden
Assistant Examiner — Monzer Chorbaji
(74) Attorney, Agent, or Firm — Juan J. Lizarraga

(57) ABSTRACT

The invention relates to a method of viral inactivation by dry heating of a virus present or potentially present in a biological product that has been dried according to the glass transition temperature.

13 Claims, 4 Drawing Sheets

Correlation Tg/ Residual moisture

Figure 1:
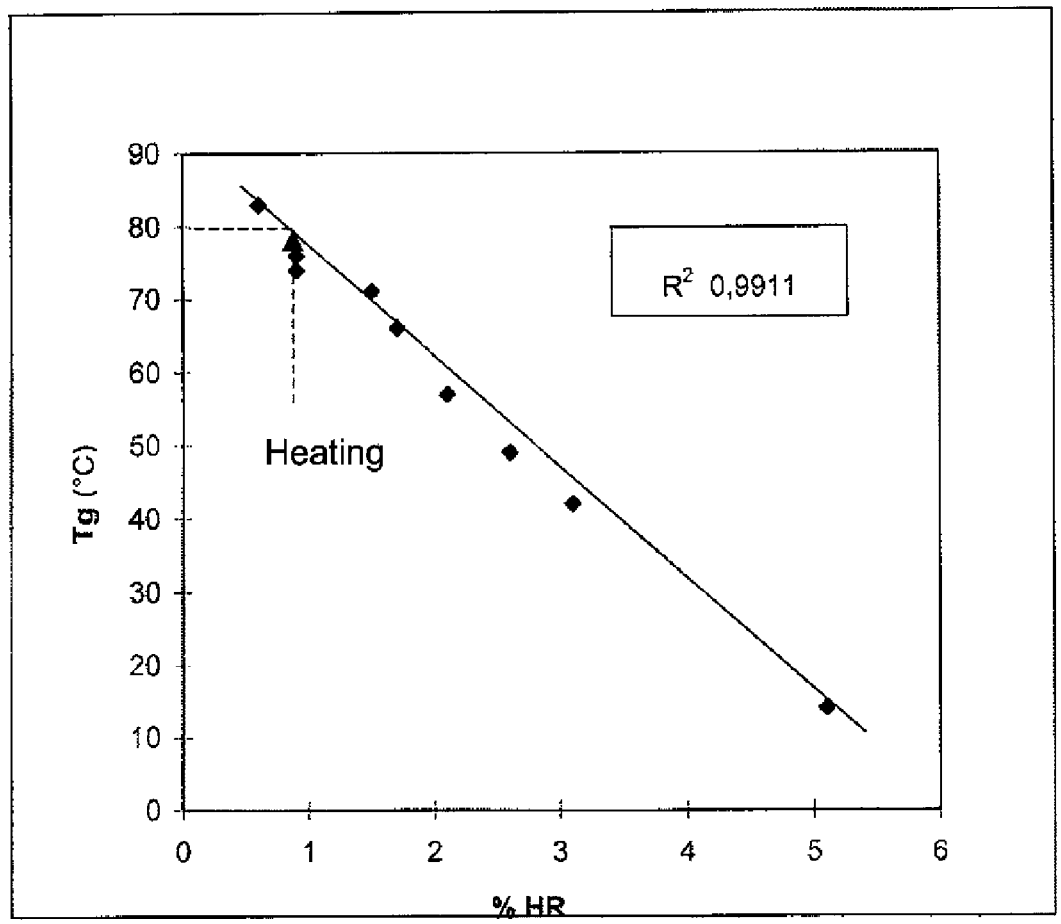

Figure 1 : Correlation Tg/ Residual moisture

INVENTION RELATES TO A METHOD OF VIRAL INACTIVATION BY DRY HEATING

The invention relates to a method of viral inactivation by dry heating.

FIELD OF THE INVENTION

The risk of viral contamination exists for any solid biological material and the latter or its derived products or the products-by-process in which such material is used, have to be submitted to viral inactivation methods to be used for therapeutic or prophylactic purposes.

In therapeutic and prophylactic domains, active substances are used which originate from biological sources, or which are likely to be contaminated by a biological source in the course of their production process.

These active substances may be proteins, peptides, polypeptides, antibodies, possibly substituted with lipid or carbohydrate groups, nucleic acids, DNA, RNA, polysaccharides, bacteria, viral particles of others.

The biological source they originate from or which is likely to contaminate them in the course of their production process might be any human or animal tissue, blood, plasma, bone, any plant tissue, any microorganism, a cell-, a virus-, a bacteria-, a yeast-, a mould- or a fungus-culture medium.

Therefore, viral reduction or inactivation steps are routinely included in the extraction steps of the active substances produced from such biological sources.

For the present invention, the by biological product is meant a product comprising an active substance produced from a biological source, and other compounds or excipients originating from the production process of said active substance.

Viral inactivation methods based on treatment with chemical products and/or heat are known to the background art. The great majority of these come from the field of blood transfusion in which the efficacy of viral inactivation is crucial since an attempt should be made to free from the possible contamination resulting from products obtained from a donor.

Heat has been recommended for inactivating HIV since the viral origin thereof has been acknowledged in particular in the blood and plasma, and blood-derived and plasma-derived products. Dry heating, i.e. heating a dry product to a temperature T for a time period t has been recommended, e.g. for lyophilised or freeze-dried concentrates of coagulation factors which have not been heated in liquid form. For example, blood Coagulation Factor VIII, extracted from human plasma used to be heated in a lyophilized form at 60° C. for 72-96 hours to make this active biological substance intended for treating hemophiliacs safe. However, inconsistent reduction in the viral inactivation by dry heating led to the abandonment of this process because several contamination cases of hemophiliacs by HIV infection were registered, despite heat inactivation.

It was therefore proposed to subject these products to so-called "severe" heat conditions, i.e. heating on the dry form at a temperature of 80° C. for 72 hours.

This viral inactivation method was subsequently validated for HIV (an enveloped virus) on the basis of clinical results obtained for a Factor VIII treated in this way (L. Winkelman et al., Severe Heat Treatment of Lyophilised Coagulation Factors Curr. Stud. Hematol. Blood Trangfus. [1989] 56: 55-69).

Treating purified proteins with a mixture of solvent and detergent is also often used to prevent the transmission of enveloped viruses by proteins derived from biological sources (Piet et al., Transfusion [1990] 30: 592-98). This treatment is effective against viruses with a lipid envelope but far less so against those without such a structure. Recently, through the use of the transmission of non-enveloped viruses through the use of a biological product treated with a solvent/detergent was described. Hepatitis A virus, a non-enveloped RNA virus, was transmitted to patients using a factor VII which had been treated with solvent/detergent (Purcell et al., Vox Sang [1994] 67: 2-7). Factor VIII was also involved in the transmission of a non-enveloped parvovirus, B19 (Lefrère et al. Lancet [1994] 343: 211-12).

Heat treatment of purified proteins has been recommended for extending spectrum of viral inactivation to non-enveloped viruses. However, heat-inactivation of non-enveloped viruses is usually more difficult than that of enveloped viruses, and often requires a longer treatment and/or higher temperatures to guarantee satisfactory inactivation. B19 has been transmitted to patients through a Factor VIII which had been dry-heated at 100° C. for 30 min. (Santagostino et al., Lancet [1994] 343:798).

It is therefore obviously important to find out how viral inactivation methods can be improved to preserve or enhance the safety of biological products.

BACKGROUND ART

Many authors tried to observe the major parameters influencing the dry-heating viral inactivation. The objective is to define a physicochemical parameter which would allow to predict whether or not a given treatment is suitable for the solid material to be treated, i.e. whether or not the process will inactivate the virus to a sufficient extent while preserving a satisfactory stability of the product. Moreover, it would be extremely interesting if this parameter could be adjustable to favour either viral inactivation or product stability.

The viral reduction factor of a viral inactivation process is defined as the factor by which the viral inactivation by dry heating is reduced, i.e. the base10 logarithm of the ratio of the viral inactivation by dry heating before the inactivation step and the viral inactivation by dry heating after the inactivation step.

The moisture content is defined as the weight quantity of matter per 100 g of the product. This is why it is expressed as a percentage of the overall weight. The traditional measure method consists in determining the decrease in weight of the product after heating at a temperature of over 100° C. until its weight remains constant.

Wilkommen et al. (Paul Ehrlich Institute) showed that, for lyophilisates containing a poor moisture level (<0.8%), Hepatitis A Virus (HAV) reduction factors obtained by heating at 80° C. for 72 hours range from 0 to 0.4 log 10, whereas for lyophilisates with a relatively high moisture level (> 0.8%), Hepatitis A virus reduction factors obtained in the same conditions are greater or equal to 4.3 log 10.

Bunch et al. (Alpha Therapeutic Corporation) showed that, for two samples of a recombinant Factor VIII Hepatitis A Virus reduction factor ($\geqq 6.9$ log 10) when heated at 80° C. for 72 hours.

Roberts P L et al. (Biologicals [2000] September; 28(3): 185-8 Comparison of the Inactivation of Canine and Bovine Parvovirus by Freeze-Drying and Dry-Heat Treatment in Two High-Purity Factor VIII Concentrates) showed the influence of the formulation of the biological product and of the resistance of the virus through the viral inactivation of two parvoviruses (bovine and canine) when two lyophilised formulations of a Factor VIII concentrate were heated at 80° C. for 72 hours.

Hart H F et al. (Vox Sang [1994] 67(4): 345-50 Effect of Terminal (Dry) Heat Treatment on Non-Enveloped Viruses in Coagulation Factor Concentrates) obtained the same Hepatitis A Virus reduction factor in Factor VIII lyophilisates heated at 80° C. for 24 hours or 90° C. for 2 hours.

Tomokiyo et al. (Vox Sang [2003] January; 84(1): 54-64 Large-Scale Production and Properties of Human Plasma-Derived Activated Factor VII Concentrate) showed, through inactivation of different viruses: CMV (Cytomegalovirus), HTV (Human Immunodeficiency Virus), BVDV (Bovine Viral Diarrhoea Virus Poliovirus), PPV (Porcine Parvovirus) in lyophilisates of Factor VIIa, that viral inactivation in lyophilisates is possible at 65° C. Heating at 65° C. for 96 hours of products with a moisture level of <1.7% shows vital reduction factors of >4 log 10 for all the viruses apart from PPV.

Patent Application EP 0 844 005 discloses that it is the residual moisture content of the desiccated biological product to be treated that is the critical element in the efficacy of viral inactivation through a dry-heating process at 80° C. for 72-77 hours. The viruses tested were HAV, Porcine Parvovirus and Pseudorabies Virus. The inventors showed that the residual moisture must be greater or equal to 0.8% to reach a viral reduction factor of $\geq$4 log 10 using this process. For residual moisture $\leq$0.8%, the mean viral reduction factor is 0.12 log 10.

TECHNICAL PROBLEM

In the light of these highly fragmentary results, it appears that no parameter was defined, the measure of which would allow to reliably determine the characteristic operational variables for a viral inactivation process based on dry heating to be used according to the biological product to be treated.

It seems nevertheless that there is some degree of consensus among the authors on the fact that the moisture level of the product to be treated plays a very important role, although said authors do not agree as regards a residual humidity level as the threshold value to obtain a satisfactory viral inactivation. In effect, it is sometimes sufficient that this value be decreased by just a few tenths to result in an incomplete inactivation.

However, in contrast to what certain authors may lead us to believe, the Applicant has shown that viral inactivation can be achieved in lyophilisates containing little residual moisture. A freeze-dried preparation of human fibrinogen with a residual moisture of 0.1% was dry heated at 77° C. for 72 hours. The reduction factors obtained for Hepatitis A virus (HAV), Human Immunodeficiency Virus (HIV), Bovine Viral Diarrhoea Virus (BVDV) and Porcine Parvovirus (PPV) are presented in Table 1.

TABLE 1

| Virus | Reduction Factor |
| --- | --- |
| HAV | 4.10 ± 0.30 |
|  | 3.75 ± 0.26 |
| HIV | 4.53 ± 0.36 |
|  | 4.62 ± 0.30 |
|  | 4.88 ± 0.28 |
| BVDV | 5.96 ± 0.40 |
|  | 5.21 ± 0.38 |
| PPV | 2.97 ± 0.43 |
|  | 2.88 ± 0.37 |

The scatter of these various observations means that the only conclusion that can be drawn is the following: the residual moisture of the product to be treated is not the determining factor for the results of viral inactivation by dry heating, but it is an important factor from which on which the determining factor would depend.

The problem is therefore to identify the measurable, multifactorial physicochemical parameter which can provide a threshold value distinguishing satisfactory from unsatisfactory viral inactivation.

SUMMARY OF THE INVENTION

The Applicant identified, in a surprising development, that this measurable physicochemical parameter is the glass transition temperature of the biological product to be treated.

Glass transition is a second-order transition, i.e. a thermal transition which involves a change in calorific capacity but not latent heat. It is characteristic of supercooled liquids which are cooled to a sufficiently low temperature quick enough to prevent crystallisation, and which therefore form a glass or an amorphous polymer, or the amorphous part of crystalline polymers which pass from a hard, brittle state to a soft, flexible state.

The glass transition temperature or Tg is the temperature at which glass transition occurs.

When a polymer is cooled below this temperature, it becomes hard and brittle, like glass—it is then said to be in a vitreous state.

Elastomeric rubbers like polyisoprene and polyisobutylene are used above their glass transition temperature, i.e. when they are rubbery, soft and flexible.

To those skilled in the art, the glass transition temperature is known to be dependent on a certain set of parameters. In the case of polymers, it depends on their molecular weight, the chain's chemical structure, and the amount of plastifying agents included.

Plastifying agents are small molecules, like salts, which intercalate between the polymer molecules and help them slide over one another, thereby facilitating their movement. The addition of a plastifying agent therefore allows to lower the glass transition temperature.

In contrast, high molecular weight molecules block the movements of polymer molecules among them and raise the glass transition temperature.

In addition, the Applicant has shown that the glass transition temperature is directly related to the residual moisture of a given lyophilisate of von Willebrand Factor (vWF).

The relationship between the lyophilisate's glass transition temperature and its residual moisture is presented graphically in FIG. 1.

The glass transition temperature of a biological product therefore depends on the nature of the active substance and the nature of the excipients: plastifying agents or not, crystalline or amorphous form the molecular weight of the excipients, and the biological product's residual moisture.

DETAILED DESCRIPTION OF THE INVENTION

The invention concerns a viral inactivation method based by dry heating a virus present or possibly present in a dried biological product, characterised by the following steps:

a) determining the glass transition temperature Tg of the dried biological product to be treated, then b) heating the dried biological product to be treated from Step a) to a dry temperature T equal to or over the glass transition temperature Tg as determined in Step a).

A dried product is a product that has been desiccated using a method familiar to those skilled in the art such as lyophilisation, vacuum-drying, pervaporation or atomisation.

In particular, a dried product is a freeze-dried product, i.e. a product first frozen and from which at least some of its water content has been subsequently sublimated under vacuum.

In effect, the Applicant observed that both the viral reduction factor and the kinetics of viral inactivation are enhanced when the heating temperature is equal to or greater than Tg.

Knowing the value of the glass transition temperature therefore makes it possible to predict if an inactivation process will be satisfactory and, if necessary, modulate the process accordingly.

The measure of the glass transition temperature of a dried biological product consists in subjecting a sample of this product to a progressive and programmed raise of the temperature of between −50° C. and +100° C., and in observing its state changes, including glass transition.

The dried biological product's thermogram, and notably its glass transition temperature is thus obtained.

The measure of the glass transition temperature has been measured, those skilled in the art—using general knowledge in the field of heat-based viral inactivation methods—will be able to judge if, in order to meet the requirement that T≧Tg:

Tg is satisfactory for the concerned virus to select a temperature T°≧Tg;
or whether Tg has to be adjusted to be able to select a T to ensure that both the sought viral inactivation and the stability of the product are satisfied.

For example, if those skilled in the art know that Tg is too low for inactivating of the virus in question at a T such as Tg≦T, and such as to keep the product stable then, the skilled persons will increase Tg such that T falls in a temperature range that is known to inactivate the virus, and the difference between T and Tg will not be so great as to cause degradation of the product.

If, on the other hand, those skilled in the art know that Tg is too high for a T≧Tg and for keeping the product stable, then Tg will be lowered before T is selected.

The dry-heating viral inactivation method for a biological product according to the invention is particularly suitable in the case of non-enveloped viruses.

This process can be used to treat a composition containing one or more blood-plasma extracted proteins as a dried biological product.

In a particular embodiment, the dry-heating temperature T is selected to allow the inactivation of a non-enveloped virus.

In a preferred manner, the glass transition temperature is increased by adding of high molecular weight excipients to the biological product or by decreasing the biological product's moisture; alternatively, it is lowered by adding salts or low molecular weight excipients to the biological product, or by increasing the biological product moisture.

In particular, the glass transition temperature is measured using a scanning differential thermoanalyser. State changes are defined as a change in calorific capacity as measured with respect to an inert product which undergoes no transformation in the temperature range under consideration.

It will be preferred that the heating temperature T of the method according to the invention should be comprised between Tg and Tg+20° C. in order to preserve a satisfactory product stability. In this range, T could be selected such as to increase the difference between Tg and T (to a maximum of Tg+20° C.) to favour the viral reduction factor and the viral inactivation kinetics, or T could be selected such as to decrease the difference between Tg and T in order to favour the product's stability.

In a particularly preferred manner, the dry-heating temperature T is selected to obtain a viral reduction factor ≧3 log 10, preferably 4 log 10.

In a particular embodiment, in a final step, the efficacy of viral inactivation in the dried treated biological product is measured and, if said efficacy is deemed insufficient, viral inactivation of the dried biological product is continued after having increased the differences between the heating temperature T and the glass transition temperature Tg.

In another particular embodiment; in a final step, the stability of the dried treated biological product is evaluated and, if said stability is deemed insufficient after having decreased viral inactivation of the dried biological product is continued after having decreased the difference between the heating temperature T and the glass transition temperature Tg.

FIGURES

FIG. 1: correlation between Tg and RM: Tg=glass transition temperature; RM=Residual Moisture FIG. 2: PR772 reduction factor after dry-heating at 62° C., depending on Tg FIG. 3: PR772 reduction factor after dry-heating at 80° C., depending on Tg FIG. 4: PPV reduction factor after dry-heating at 80° C., depending on Tg FIG. 5: PPV, HAV, BVDV, PR772, Phi 174 reduction factors at T=Tg=80° C.

Figure 6:
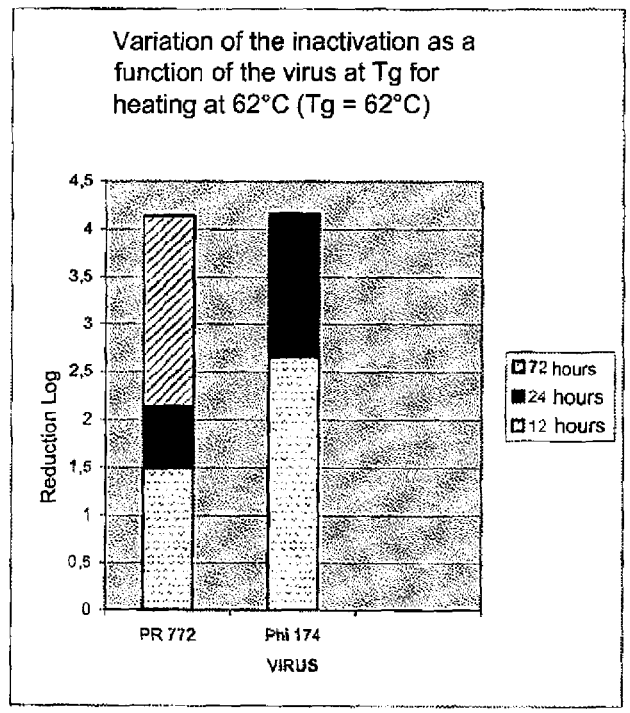

FIG. 6: PPV, HAV, BVDV, PR772, Phi174 reduction factors at T=Tg=62° C.

EXAMPLES

Example 1

Inactivation of Bacteriophage PR772 in Lyophilisates by Dry-Heating

The physical properties of the lyophilisates are modified in order to modulate the glass transition temperature (Tg).

Glass transition temperature is determined using a scanning differential thermonalyser. The temperature of the scanning differential thermonalyser is calibrated using indium (Tm 156.6° C.) and n-octadecane (Tm 28.2° C.). Samples are subjected to temperatures of from −50°G to 130° C. at a rate of change of 20° C./min. Liquid nitrogen is used to conduct the experiments at a temperature which is below room temperature. The glass transition temperature was taken as the median point of the endothermic change in the apparent specific heat. Two measurements are carried out and the mean is taken as the Tg.

Heating is performed at either a temperature lower than Tg (i.e. in the solid, vitreous state), or a temperature about 20° C. above Tg (i.e. in the viscoelastic [rubbery] state).

All the lyophilisates have a water content of less than 1%.

Water content is determined using the Karl-Fisher method, well-known to those skilled in the art, based on the reaction between water and iodine.

Formulation of Product A (pH 7.0±0.5)

| | |
|---|---|
| glycine | 7.5 g/l |
| lysine HCl | 5.5 g/l |
| CaCl2 | 0.15 g/l |
| mannitol | 40 g/l |
| sucrose | 50 g/l |
| FVIII | 100 IU/ml |

Product A has a Tg of 62° C.

Product B has the same formulation as Product A with added NaCl. This allowed to decrease Tg to about 40° C. (with the same moisture RM).

C is a freeze-dried vWF concentrate, and D is a freeze-dried human fibrinogen.

Formulation of Product C (pH 7.0±0.5)

| trisodium citrate | 10 mM |
|---|---|
| CaCl2 | 1 mM |
| glycine | 5 g/l |
| arginine HCl | 40 g/l |
| albumin | 10 g/l |
| vWF | 100 IU/ml |

Formulation of Product D (6.8<Ph<7.2)

| fibrinogen | 11 to 20 g/l |
|---|---|
| arginine hydrochloride | 40 g/l |
| isoleucine | 10 g/l |
| glycine | 2 g/l |
| lysine monohydrochloride | 2 g/l |
| trisodium citrate.2 H20 | 2.5 g/l |

Products C and D have respective Tg values of 80° C. and 90° C.

The reduction factor for bacteriophage PR772 is measured at 12, 24 and 72 hours, for heating at 62° C. and 80° C.

Viral inactivation by dry heating is calculated using the Spearman Kärber equation as described in the Federal Gazette No 84, May 4, 1994, and in Schmidt, N. J. & Emmons, R. W. (1989) in Diagnostic Procedures for Viral, Rickettsial and Chlamydial Infection, $6^{th}$ Edition.

The reduction factor is the resultant of the ratio between the viral inactivation by dry heating/ml before dry-heat treatment and the viral inactivation by dry heating/ml after dry-heat treatment.

Figure 2:
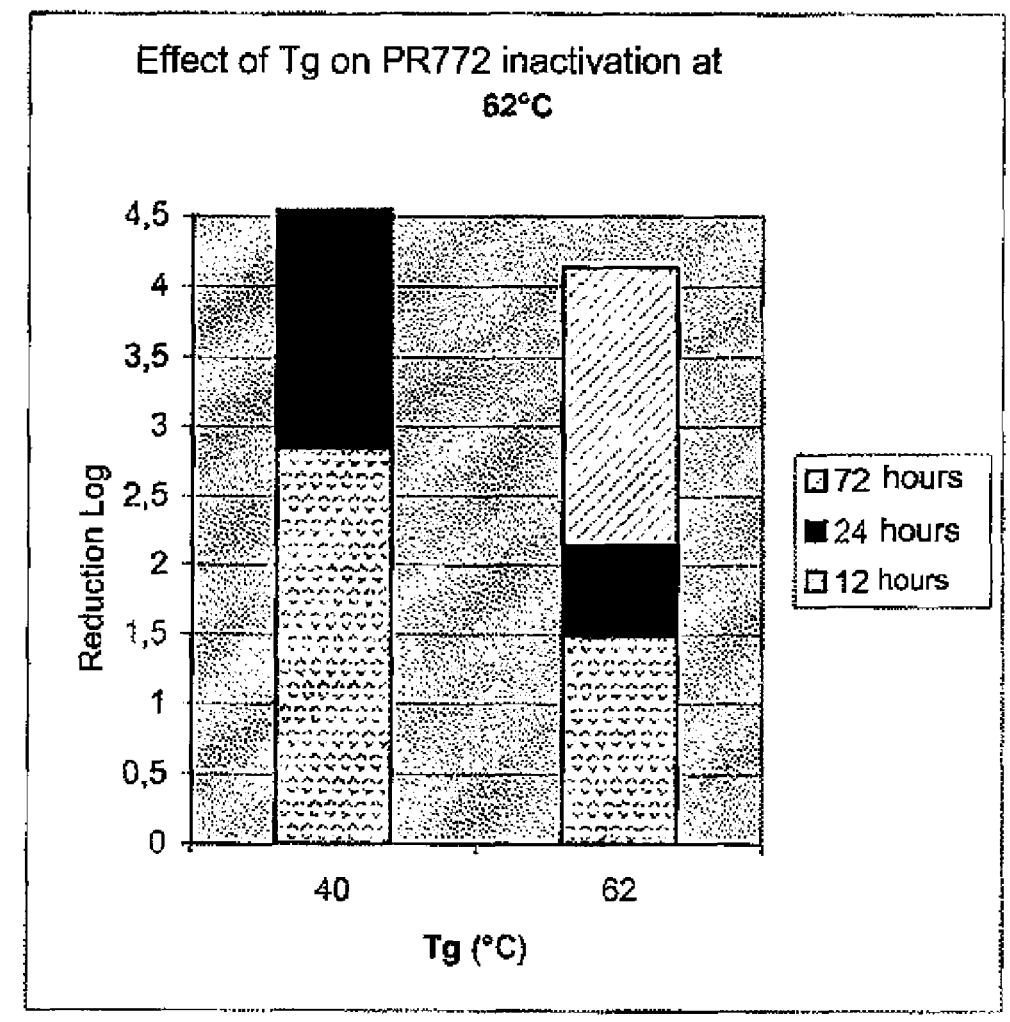
Figure 3:
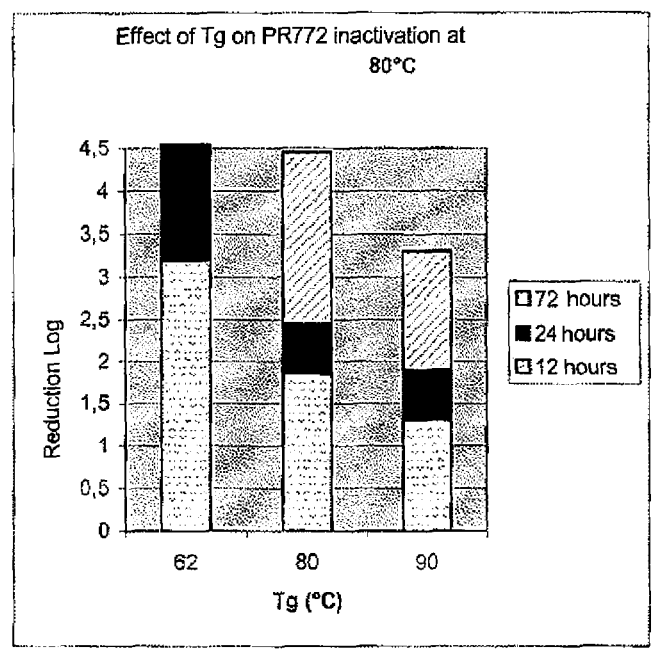

The results are presented in graph form in FIGS. 2 and 3.

It can be seen that:

for heating at T=80° C.:

1. of Product A for which a Tg= 62° C. (T−Tg≈20° C.), the inactivation is very fast and the reduction factor reached 4 log 10 in less than 24 hours 2. of Product C for which Tg=T, the reduction factor reaches 4 log 10 after 72 hours 3. of Product D for which Tg=90° C., the reduction factor reaches 4 log 10 after 72 hours for heating to T= 62° C.:

1. of Product A for which Tg=T the reduction factor reaches 4 log 10 after 72 hours 2. of Product B for which Tg=40° C. (T−Tg≈20° C.), the inactivation kinetics is very fast and the reduction factor reaches 4 log 10 in less than 24 hours Example 2

Inactivation of PPV in Lyophilisates by Dry-Heating

The PPV reduction factor is measured at 12, 24 and 72 hours, for heating at 80° C. in lyophilisates with a Tg= 80° C. or 90° C.

Figure 4:
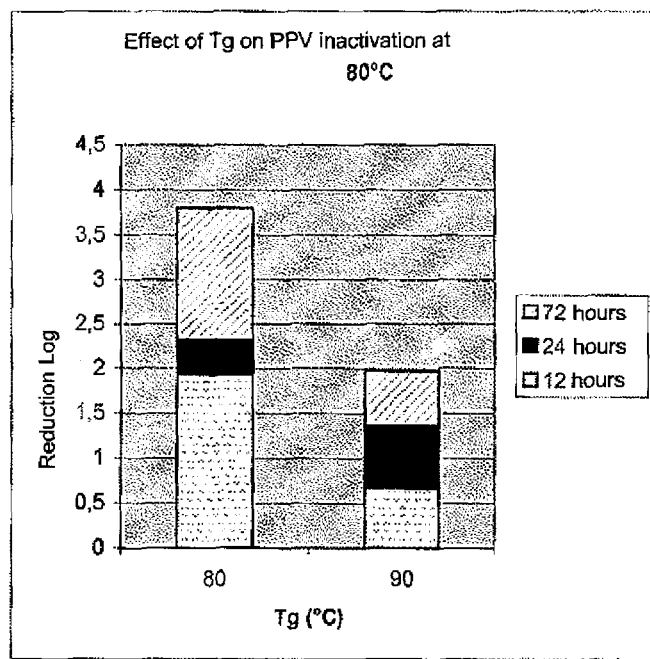

The results are presented in graph form in FIG. 4.

It can be seen that for heating at T=80° C.

when Tg=T, the reduction factor is close to 4 log 10 when T<Tg, the reduction factor is relatively low, of the order of 2 log 10.

Example 3

Inactivation of PPV, HAV, BVDV, PR772 and Phi174 in Lyophilisates by Dry Heating at T=Tg The reduction factor for PPV, HAV, BVDV, PR772 and the bacteriophage Phi174 is measured at 12, 24 and 72 hours for heating at T=Tg=80° C. (in a lyophilisate with a Tg=80° C.) or at T=Tg=62° C. (in a lyophilisate with a Tg=62° C.).

Figure 5:
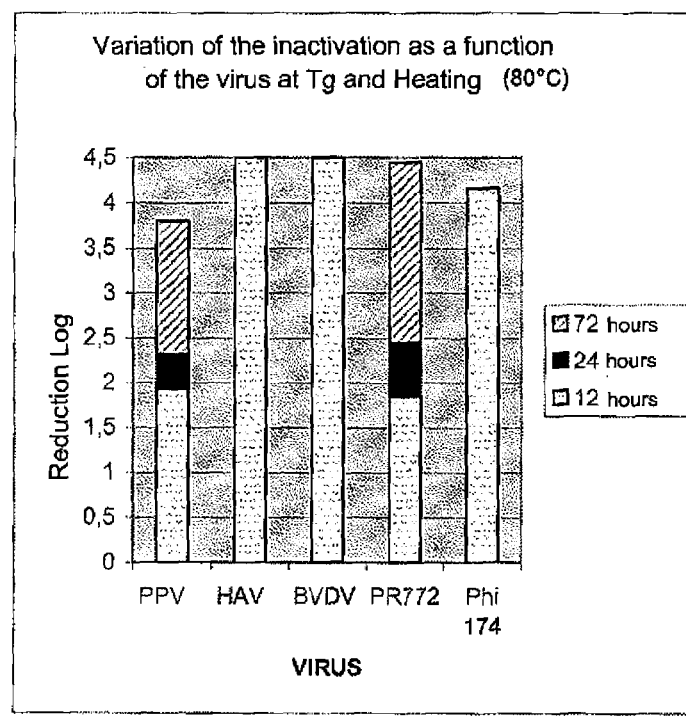

The results are presented in graph form in FIGS. 5 and 6.

It can be seen that, for weak resistant viruses, namely HAV, BVDV, Phi174, heating to T=Tg is sufficient to reach a reduction factor of 4 log 10 as soon as from 24 hours.

By contrast, for more resistant viruses, namely PPV and PR772, the heating time has to be prolonged to 72 hours to reach a reduction factor close to 4 log 10.

As a result, for these more resistant viruses, since the aim is their inactivation, the viral reduction factor and the rate of viral inactivation can be enhanced by increasing the heating temperature T or by lowering the product's Tg, in order to increase the differential between T and Tg.

Further, the range T−Tg≧20° C. will be preferred to enhance the rate of viral inactivation or the range T−Tg≦20° C. will be preferred to enhance the product stability.

Example 4

Effect of Heating at 80° C. for 72 Hours on a vWF Lyophilisate's Physicochemical Properties as a Function of its Glass Transition Temperature Three vWF lyophilisates with different glass transition temperatures were heated at 80° C. for 72 hours. Various parameters—the lyophilisate's appearance, its dissolution time and the appearance of the resultant solution—were observed.

The results are presented in Table 2.

TABLE 2

| % RM | 0.9 | 1.7 | 3.1 |
|---|---|---|---|
| Tg (° C.) | 74 | 66 | 42 |
| vWF: Rco (IU/ml) | 140 | 120 | 105 |
| Appearance of the lyophilisate | normal | slightly retracted | very retracted |
| Dissolution time (s) | 15 | 35 | 75 |
| Appearance of the solution | clear | clear | clear |

It can be seen that a heating temperature T≧Tg and T−Tg≦20° C. allows to conserve a satisfactory product stability even though the selected temperature leads to a state change from the vitreous state to the rubbery state.

It can also be seen that the too important differential between the heating temperature and Tg, 38° C. here, is unfavourable for the product stability.

In consequence, the closer T is selected to Tg, the greater the product stability is favoured.

The invention claimed is:

1. Viral inactivation method by dry heating, targeting of a virus present or possibly present in a dried active substance produced from a biological source, comprising other compounds or excipients originating from the production process of said active substance, wherein the steps are:

a) determining the glass transition temperature Tg of the said dried active substance to be treated, then b) heating the said dried active substance to be treated from Step a) at a dry heating temperature T comprised between Tg and Tg+20° C., wherein T is selected such as to increase the differential between Tg and T (up to Tg+20° C.) to enhance viral reduction factor and the rate of viral inactivation.

2. Method according to claim 1, wherein the glass transition temperature Tg of the dried active substance is adjusted prior to dry-heating.

3. Method according to claim 1 or 2, wherein the dried active substance is a lyophilisate.

4. Method according to claim 1, wherein the dried active substance is a composition containing one or more proteins extracted from blood-plasma.

5. Method according to claim 1, wherein the dry-heating temperature T is selected to allow the inactivation of a non-enveloped virus.

6. Method according to claim 1, wherein the glass transition temperature is increased by either adding high molecular weight excipients to the biological product or reducing the biological product's moisture.

7. Method according to claim 1, wherein the glass transition temperature is lowered by adding salts or low molecular weight excipients to the biological product or by increasing the biological product's moisture content.

8. Method according to claim 1, wherein Tg is measured using a scanning differential thermoanalyser.

9. Method according to claim 1, wherein the dry heating temperature T is selected to obtain a viral reduction factor $\geq 3$ log 10.

10. Method according to claim 1, wherein the dry heating temperature T is selected to obtain a viral reduction factor of $\geq 4$ log 10.

11. Method according to claim 1, wherein T is selected to reduce the differential between Tg and T to favour active substance stability.

12. Method according to claim 1, wherein, in a final step, the efficacy of viral inactivation in the treated, dried active substance is measured and, if said efficacy is deemed insufficient, viral inactivation of the dried active substance is continued, after having increased the differential between said heating temperature T and said glass transition temperature Tg.

13. Method according to claims 1, wherein, in a final step, the stability of the treated dried active substance is evaluated and, if said stability is deemed insufficient, viral inactivation of the dried active substance is continued, after having reduced the differential between said heating temperature T and said glass transition temperature Tg.

* * * * *